United States Patent [19]

Hearn et al.

[11] 4,279,724
[45] Jul. 21, 1981

[54] PREPARATIVE ELECTROFOCUSING IN FLAT BED GRANULATED POLYSACCHARIDE GELS

[76] Inventors: Milton T. W. Hearn, P.O. Box 913, Dunedin, New Zealand; Ross L. Prestidge, University Station, Birmingham, Ala. 35294

[21] Appl. No.: 58,686

[22] Filed: Jul. 18, 1979

[51] Int. Cl.³ .............................. G01N 27/26
[52] U.S. Cl. .................. 204/180 G; 204/180 R; 204/299 R; 23/230 B; 424/12
[58] Field of Search ........... 204/180 G, 180 S, 299 R; 424/12; 23/230 B

[56] References Cited

U.S. PATENT DOCUMENTS

4,139,440  2/1979  Chrambach et al. ............ 204/180 G

*Primary Examiner*—Arthur C. Prescott
*Attorney, Agent, or Firm*—Murray and Whisenhunt

[57] ABSTRACT

Methods are described for the generation of natural pH gradients in layers of granulated gels using mixtures of amphoteric or amphoteric non-amphoteric buffer reagents. Because of the favorable characteristics of these flat bed systems, high voltage gradients (20–50 V/cm) can be used for the electrofocusing experiments. Linear or step pH gradients can be formed depending on the choice of buffer system used. Buffer systems, suitable for the preparative electrofocusing of proteins over the pI ranges of 4.0–6.0, 4.5–8.0, 5.0–8.5 and 6.0–8.5 are described.

19 Claims, 16 Drawing Figures

PREPARATIVE ELECTROFOCUSING IN FLAT BED GRANULATED POLYSACCHARIDE GELS

BACKGROUND OF THE INVENTION (1) Field of the Invention

This invention relates to preparative electrofocusing in flat bed granulated polysaccharide gels.

(2) Descriptions of the Prior Art

The technique of electrofocusing is used to separate protein mixtures on the basis of differences in net charge in a stable pH gradient. If an ampholyte mixture is distributed along a support between two electrodes and a direct current applied through the ampholyte mixture at equilibrium the electro-migration of ampholytes towards the electrodes and the opposing diffusion flow are balanced with the various ampholyte components distributed in the support from anode to cathode in order of increasing pI. The concentrations of each component will be distributed approximately in gaussian fashion about their respective pIs.

The technique was discussed by Svensson (*Acta Chem. Scand.* 15 (1961) 325-341; *Acta Chem. Scand.* 16 (1962) 456-466). It was suggested by Svensson that all ampholytes with pI-pK, values bigger than 2.5 units (which includes all neutral amino acids) were useless as carrier reagents and those with pI-pK, values between 1.5 and 2.5 units were poorer carriers. Subsequently there were developed a series of synthetic polyaminopolycarboxylic acids sold under the trade mark "Ampholines" which had advantages as carrier ampholytes in comparison with known ampholytes at the time. However these ampholytes are very costly and have a tendency to strongly complex with both acidic and basic molecules modifying their pattern obtained. Also they tend to bind to stains commonly used for the localisation of protein zones giving rise to staining difficulties in the detection of minor protein components.

Chrambach et.al. (*Anal. Biochem.* 74 145 (1976) have used systems containing polyacrylamide gel rods as the supporting medium and more common buffers as ampholytes. However, these studies have been directed primarily at microanalytical applications and are of limited value for preparative separations.

It is an object of this invention to provide an electrofocusing system which can be used for preparative electrofocusing of protein mixtures. The method described in this invention permits large sample loadings of mixtures of proteins and other biological substances and the focused zones can be easily recovered in high yield without significant loss of biological activity.

BRIEF SUMMARY OF THE INVENTION

Accordingly the invention may be said broadly to consist in a preparative electrofocusing system comprising a flat bed granular polysaccharide gel suspended in a buffer mixture, a catholyte at one side of said flat bed gel and an anolyte at the other side thereof, a source of direct current between said catholyte and anolyte, said buffer comprising a combination of at least four amphoteric members selected from the group consisting of Glu, LA, PA, Pyr, MES, ADA, Bistris, MOPS, ACES, Imid, HEPES, TES, EPPS, TEA, TAPS, Glygly, Tricine, Bicine, Asn, Tris, AEPD, AMP, NH₃, His, Gly, Tau, β-Ala, EA, Lys, TA, GACA and GABA.

EXAMPLE 1

General Procedure of focusing experiments (i) Focusing was carried out on a Pyrex flat bed apparatus using granulated polysaccharides such as washed Sephadex* G75 or G200 superfine (3-5 g), suspended in a buffer containing components selected from Table 1 herein. The gel tray of an LKB Multiphor (trademark) electrophoresis apparatus was filled with this suspension and excess buffer removed by filter paper strips at each end of the gel bed until the surface of the gel acquired a granular appearance. The dimensions of the gel bed were 240×110×7 mm. Strips of paper soaked in the appropriate electrode solutions (0.2 M KOH for the cathode; 0.2 M $H_2SO_4$ for the anode) were placed in slots formed by removal of gel at each end of the bed.* The temperature of the gel was maintained during the electrofocusing at ca. 18°, using a water cooled contact plate. The voltage was regulated such that the power dissipated in the gel was limited to ca. 15 W. At the time intervals indicated below the gel bed was sectioned and the pH of each section was, after the addition of water (2 cm³), measured with a glass electrode on a Radiometer PHM64 meter.**** For convenience and reproducibility in measuring the pH and voltage gradients, the gel bed was divided into 30 equivalent sections using a calibrated grid. Voltage, current and resistivity were determined during and at the completion of the focusing experiments. In experiments utilising proteins, these were visualised in focused gel slabs by the paper print technique of Radola ([1973] *Biochim. Biophys Acta*, 295, 412-428).

*"SEPHADEX"—Trademark for a dry, insoluble powder composed of macroscopic beads which are synthetic, organic compounds derived from the polysaccharide dextran. The dextran chains are cross-linked to give a three dimensional network and the functional ionic groups are attached to the glucose units of the polysaccharide chains by ether linkages.
**Larger gel beds can be used with appropriate power supplies.
***Other alkaline hydroxides can be used as catholytes whilst phosphoric and strong organic acids can be used as anolytes at similar molarities.
****Alternatively, the pH of the gel bed was measured with a LKB 2117-111 contact pH electrode.

(ii) Reagents

All the buffer compounds and commercial protein samples were obtained from Sigma Chemicals Co., St. Louis, Miss., U.S.A. Buffer mixtures were made up in distilled water (X=$10^{-7}$ ohm$^{-1}$ cm$^{-1}$) to the appropriate concentration, the pH adjusted where necessary with 1 M NaOH or 1 M $H_2SO_4$. The buffer mixtures could be stored at 4° C. for at least one month.

TABLE 1

| Amphoteric and Non Amphoteric Reagents arranged in order of increasing pKa | | | |
|---|---|---|---|
| Reagent | Abbreviation | pKa | pI |
| Glutamic acid | Glu | 2.2 | 3.2 |
| Lactic acid | LA | 3.8 | — |
| Propionic acid | PA | 4.9 | — |
| Pyridine | Pyr | 5.5 | — |

TABLE 1-continued

Amphoteric and Non Amphoteric Reagents arranged in order of increasing pKa

| Reagent | Abbreviation | pKa | pI |
|---|---|---|---|
| 2-(N-Morpholino)-ethane sulphonic acid | MES | 6.4 | 3.8 |
| N-2-Acetamidoiminodi-acetic acid | ADA | 6.6 | 4.5 |
| Bis-(2-Hydroxyethyl)-imino-tris-hydroxymethyl methane | Bistris | 6.8 | — |
| 3-(N-Morpholino) propane-sulphonic acid | MOPS | 7.2 | 4.3 |
| N-(2-Acetamido)-2-amino ethanesulphonic acid | ACES | 7.3 | 4.2 |
| Imidazole | Imid | 7.46 | — |
| N-2-Hydroxyethylpiper-azine-N-2-ethane sulphonic acid | HEPES | 7.55 | 4.5 |
| N-tris(Hydroxymethyl) methyl-2-aminoethane sulphonic acid | TES | 7.9 | 4.5 |
| N-2-Hydroxyethylpiper-azinepropanesulphonic acid | EPPS | 8.0 | 4.7 |
| Triethanolamine | TEA | 8.35 | — |
| N-tris(Hydroxymethyl)methyl-aminopropanesulphonic acid | TAPS | 8.4 | 4.9 |
| Glycinylglycine | Glygly | 8.4 | 5.6 |
| N-tris(Hydroxymethyl)-methylglycine | Tricine | 8.6 | 5.2 |
| N,N-bis(2-Hydroxyethyl)-glycine | Bicine | 8.74 | 5.3 |
| Asparagine | Asn | 8.8 | 5.4 |
| N-tris(Hydroxymethyl)amino-methane | Tris | 8.8 | — |
| 2-Amino-2-ethyl-1,3-prop-anediol | AEPD | 8.8 | — |
| 2-Amino-2-methyl-prop-anol | AMP | 8.8 | — |
| Ammonia | $NH_3$ | 9.25 | — |
| Histidine | His | 9.3 | 7.6 |
| Glycine | Gly | 9.6 | 6.0 |
| 2-Aminoethanesulphonic acid | Tau | 9.7 | 4.8 |
| β-Alanine | β-Ala | 10.2 | 6.9 |
| Ethanolamine | EA | 10.4 | — |
| Lysine | Lys | 10.5 | 9.8 |
| Triethylamine | TA | 10.7 | — |
| ε-Aminocaproic acid | GACA | 10.8 | 7.6 |
| γ-Aminobutyric acid | GABA | 11.3 | 7.5 |

EXAMPLE 2

Figure 1:
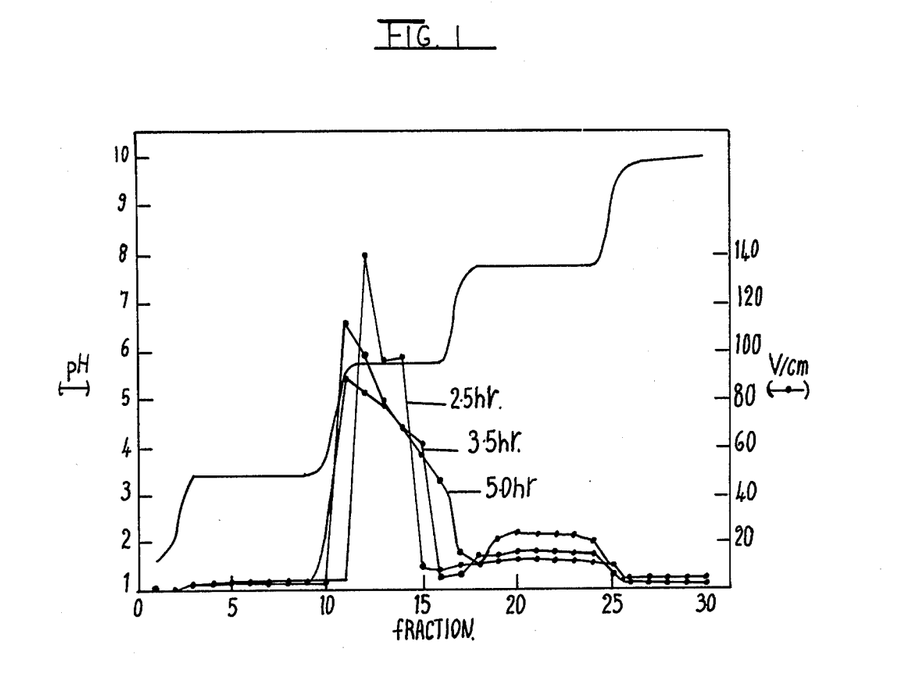
FIGS. 1-4, 6-15 are plots showing the pH gradient formed in a gel containing buffer mixtures according to the invention and superimposed thereon are shown the volts/cm change along the gel as explained more fully in the examples.

A 10 mM solution of each of the following buffers was made: Glu, Gly-Gly, His and Lys. A Sephadex G200 superfine (3.0 g) gel bed was prepared in this buffer by the procedure of example 1, and focusing was carried out at an initial power setting of 15 W. After 5 hours a constant current of 3.0 mA was reached. FIG. 1 shows the pH gradient formed in the gel containing this buffer mixture (system 1) and the Volts/cm change along the gel after 2.5, 3.5 and 5 hours.

EXAMPLE 3

Figure 2:
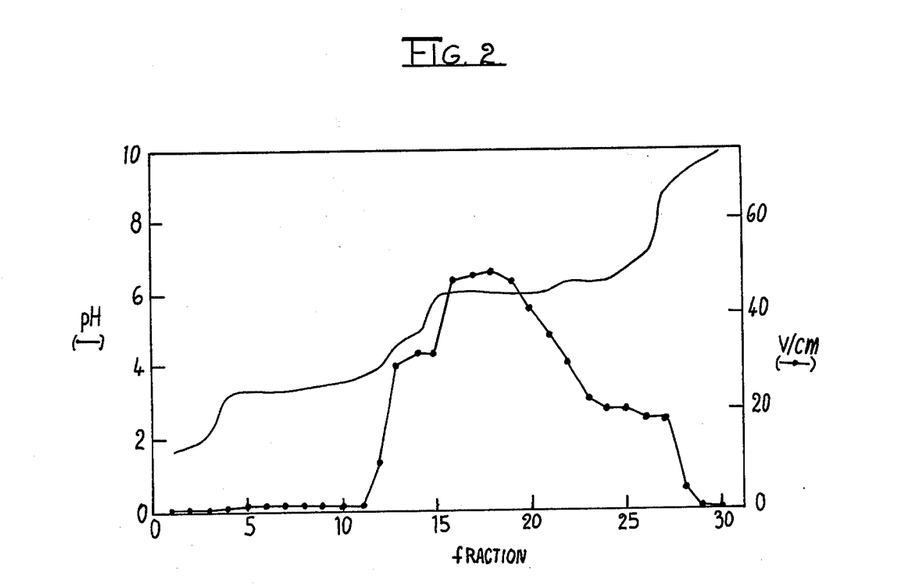

(a) A Sephadex G200 superfine (4.0 g) gel containing the amphoteric buffer mixture: 10 mM each of Glu, Tau, Gly, GABA, Lys, (system 2) was prepared by the procedure of example 1. After ca. 20 hours a steady state was reached with the current constant at 2 mA. The pH and voltage gradients measured 22.5 hours are shown in FIG. 2.

Figure 3:
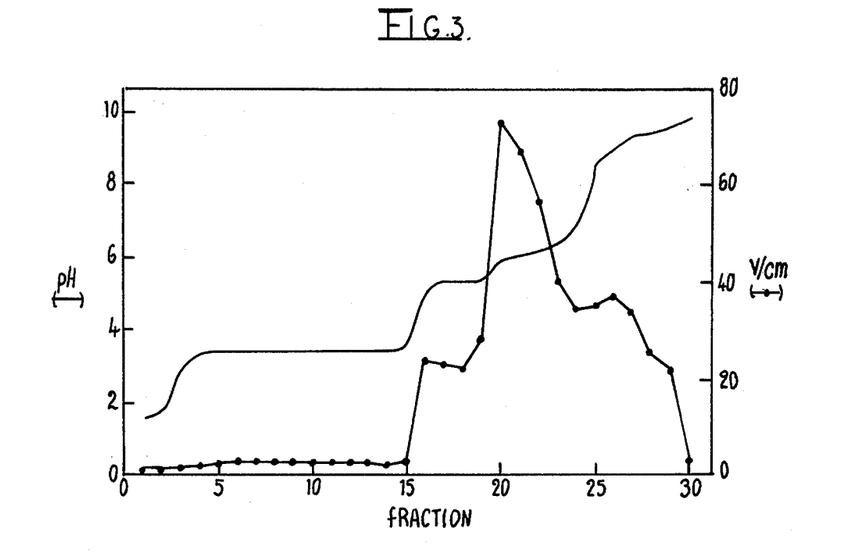

(b) FIG. 3 shows a similar focusing experiment except that Gly was deleted from the buffer system 2. The pH and voltage gradients of this new buffer (system 3) were determined at 20 hours. The current had decayed from an initial 50 mA to a steady state 2 mA at the completion of the experiment.

EXAMPLE 4

Figure 4:
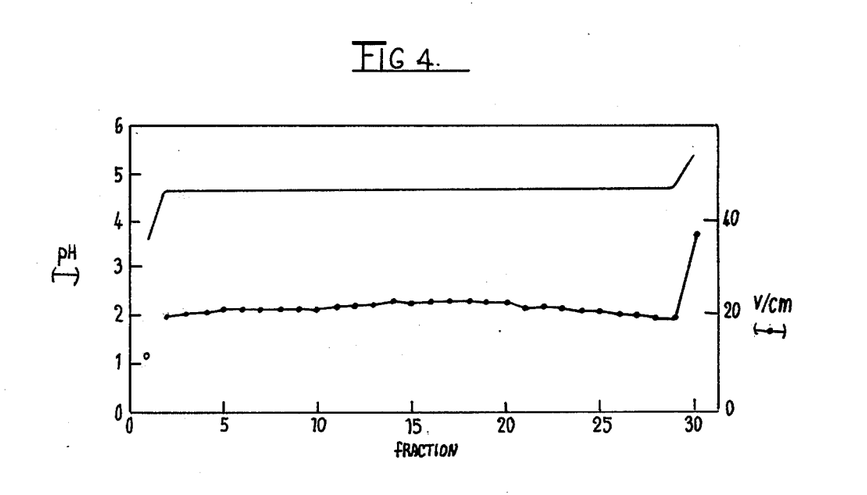
Figure 5:
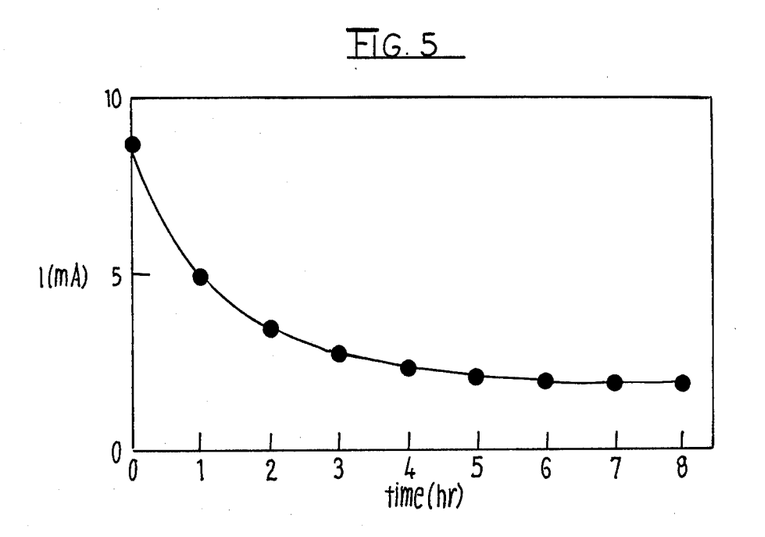
FIG. 5 is plot of current against time employing the buffer mixture described in Example 5.

(a) The pH and voltage gradient generated on a Sephadex-G75 superfine (3 g) gel bed with a narrow range amphoteric buffer mixture composed of 10 mM each of MES, ACES, TES, Tricine and Bicine and 5 mM of Tau, pH 4.33 (system 4) prepared by the procedure of example 1, is depicted in FIG. 4. The rate of decrease of the current at constant voltage is shown in FIG. 5.

Figure 6:
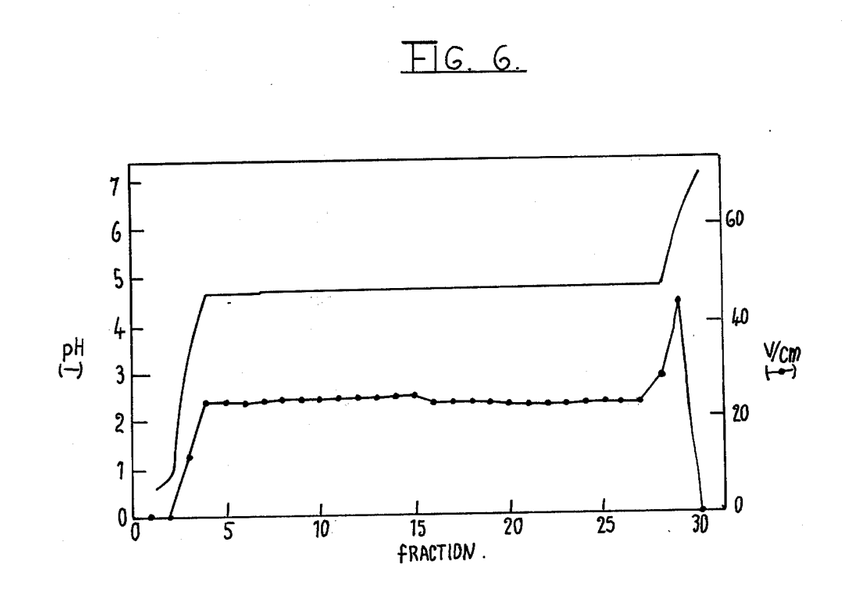

(b) Using the same buffer components and focusing conditions, but replacing the conventional anolyte and catholyte buffers (0.2 M $H_2SO_4$ and KOH respectively) with sufficient 1 M HCl and 1 M NaOH to titrate all the buffers, resulted in only a small compression of the pH gradient along the gel bed. FIG. 6 shows the result of this experiment.

Figure 7:
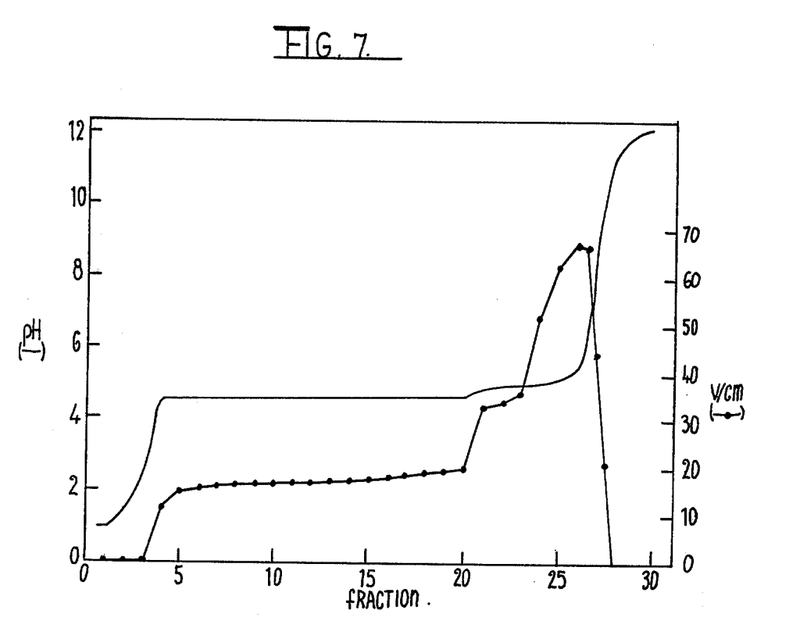

(c) The effect of adjusting the pH of the buffer mixture from pH 4.3 to pH 6.6 with NaOH (system 5) on the resultant pH and voltage gradient following focusing for 5½ hours is depicted in FIG. 7. In this case the prominent pH plateau, characteristic of this buffer system again was at pH 4.6 but a second step at pH 4.9 has appeared.

Figure 8:
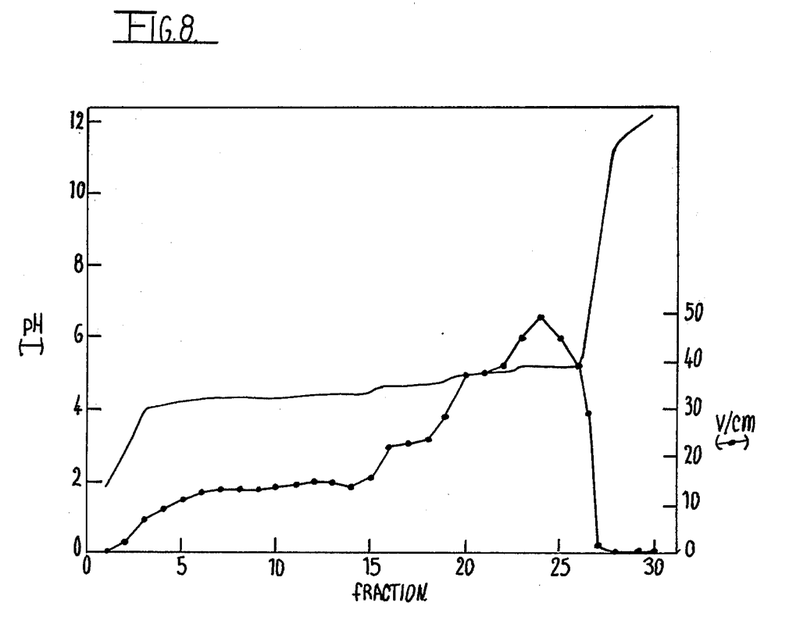

(d) Further adjustment of the pH to pH 7.1 (system 6) using the buffer system 4 resulted in the emergence of several new steps in the pH gradient (FIG. 8).

Figure 9:
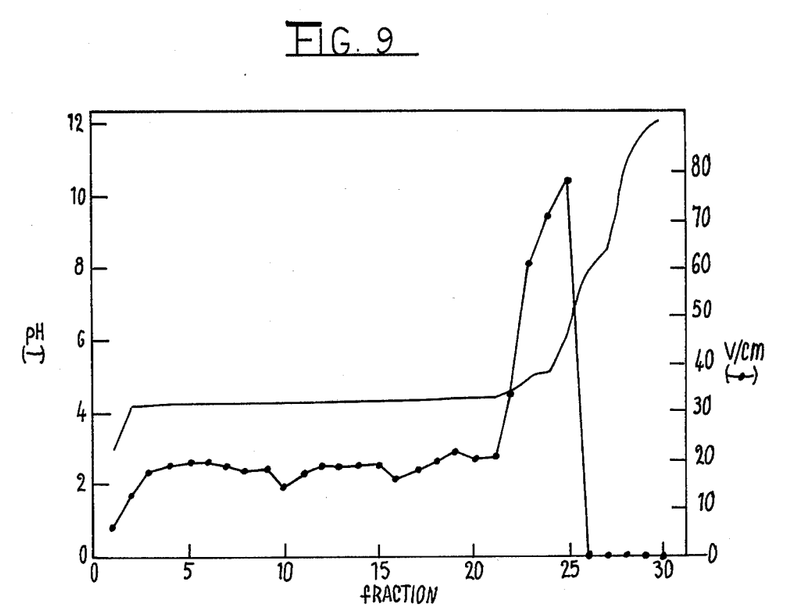

(e) By decreasing the concentration of the more acidic components it was anticipated that similar step discontinuities could be induced in the low pH end of the gradient. However, the effect of reducing the concentration of ACES and TES from 10 mM to 2 mM (system 7), all other conditions being held the same as experiment (iii d), was to uniformly lower the level of the pH plateau from pH 4.6 to pH 4.3. FIG. 9 shows the pH and voltage gradient generated with the lower concentration of ACES and TES.

Figure 10:
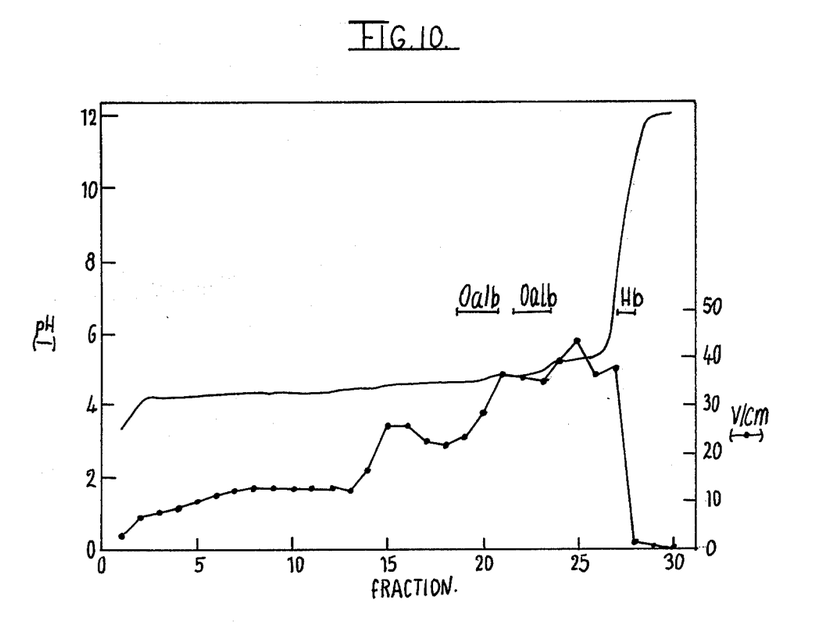

(f) A sample of crude ovalbumin (100 mg) was dissolved in the narrow range buffer mixture comprising 10 mM each of MES, ACES, TES, Tau, Tricine and Bicine (system 8) and loaded onto a Sephadex G200 superfine (3 g) gel bed containing the same buffer mix. After 24 hours, (FIG. 10) the protein bands were visualised by the Radola technique (see example 1). On recovery of the protein bands, ovalbumin (61 mg) was obtained from the focused gel in the pH range 4.6–4.8 (cf. pI 4.52–4.98 (14). A minor protein was recovered from the gel in the pH range 4.9–5.0 of the gradient.

EXAMPLE 5

Figure 11:
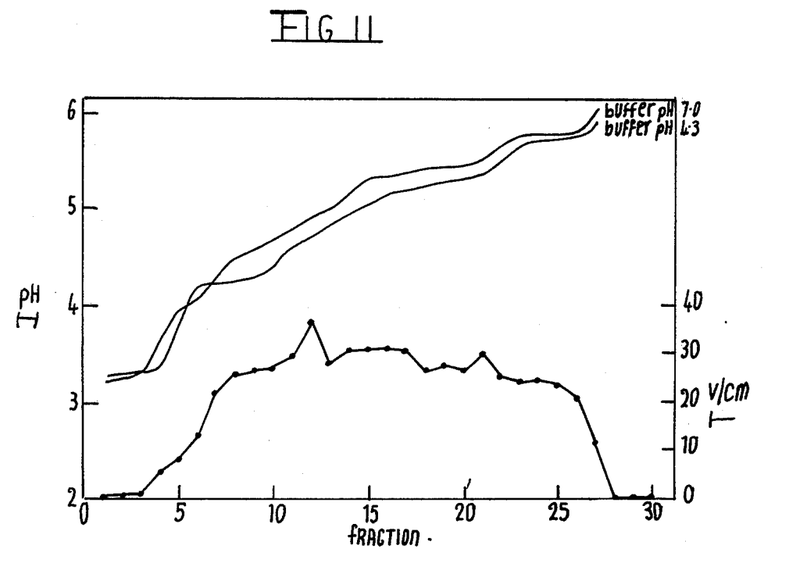

The amphoteric buffer system: Glu, MES, ACES, MOPS, HEPES, TES, EPPS, TAPS, Tau, Tricine, Bicine, Asn, GlyGly, at a concentration of 10 mM except Tau (5 mM) containing B-mercaptoethanol (10 mM) (system 9) generated, on a Sephadex G200 superfine (3 g) gel bed, the pH and voltage gradient shown in FIG. 11. The effect of pH adjustment of the buffer mixture from 4.3 to 7.0 is also depicted in FIG. 11. The gradient was stable for at least 48 hours.

EXAMPLE 6

Figure 12:
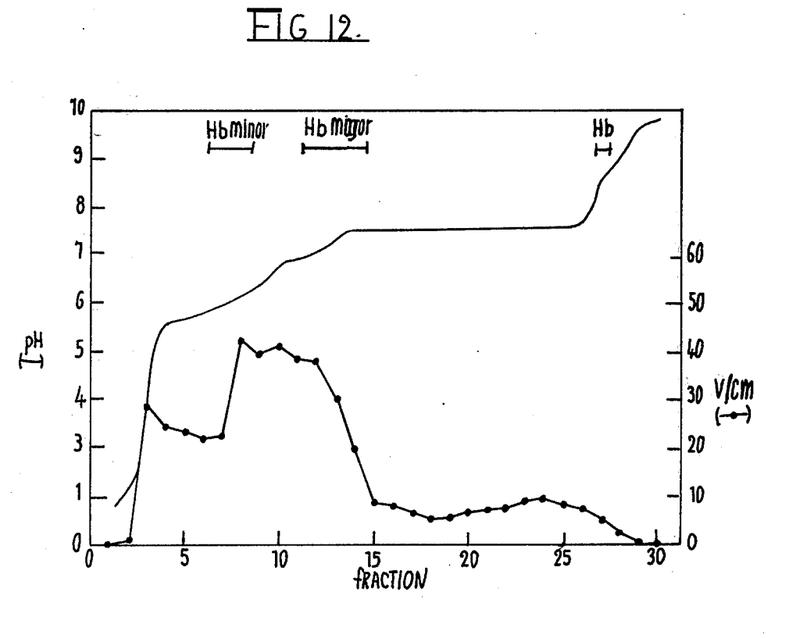

The pH gradient formed in a Sephadex G200 superfine gel bed on electrofocusing a buffer mixture of 10 mM each of Glygly, Gly, B-Ala, GABA, GACA, His and Lys, pH 7.1 (system 10) is shown in FIG. 12. The voltage gradient determined after 20 hours is superimposed. A mixture of haemoglobin and myoglobin (20 mg each) was resolved into discrete bands at the positions indicated. This buffer system provides a useful focusing range from pH 6 to 8.5. Some denaturation of the haemoglobin zones, presumably due to local heating or oxidation, was found.

EXAMPLE 7

Figure 13:
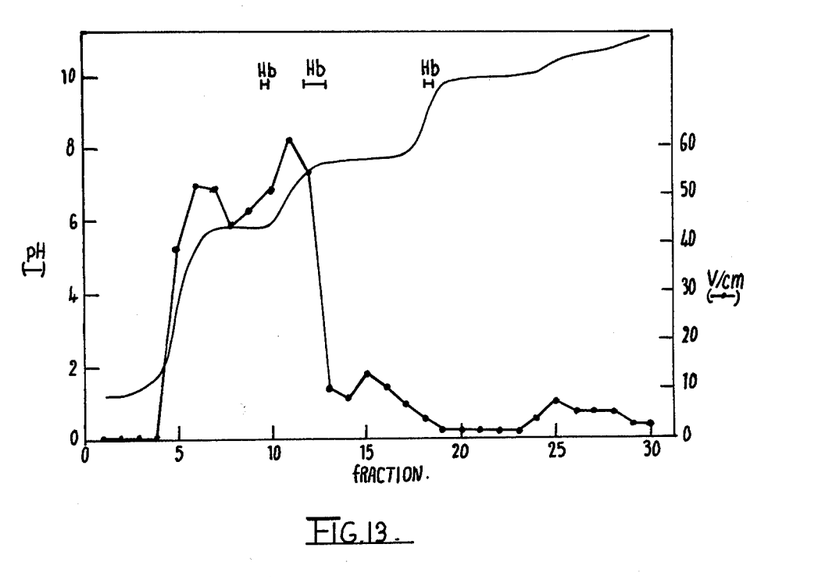

In an attempt to extend the pH range of system 10, the effect of a combination of basic non-amphoteric buffers was examined. The pH and voltage gradient formed on a Sephadex G200 superfine gel bed with a buffer mixture containing 10 mM of system 11 together with Tris, AEPD, $NH_3$, AMP and TEA (system 11) is shown in FIG. 13. Although a mixture of haemoglobin and myoglobin were adequately resolved with this buffer system, the low conductivity, and resultant local heating obtained over the pH range 6-8, resulted in extensive denaturation of the haemoglobin.

EXAMPLE 8

The narrow range buffer systems of examples 1-7 covered the pH ranges 4-6 and 6-8.5. Buffer systems which could be used to establish a stable pH gradient over the range 4.5-8.0 were also examined i.e. a 'standard' buffer adequate for the resolution of many acidic and neutral proteins.

Figure 14:
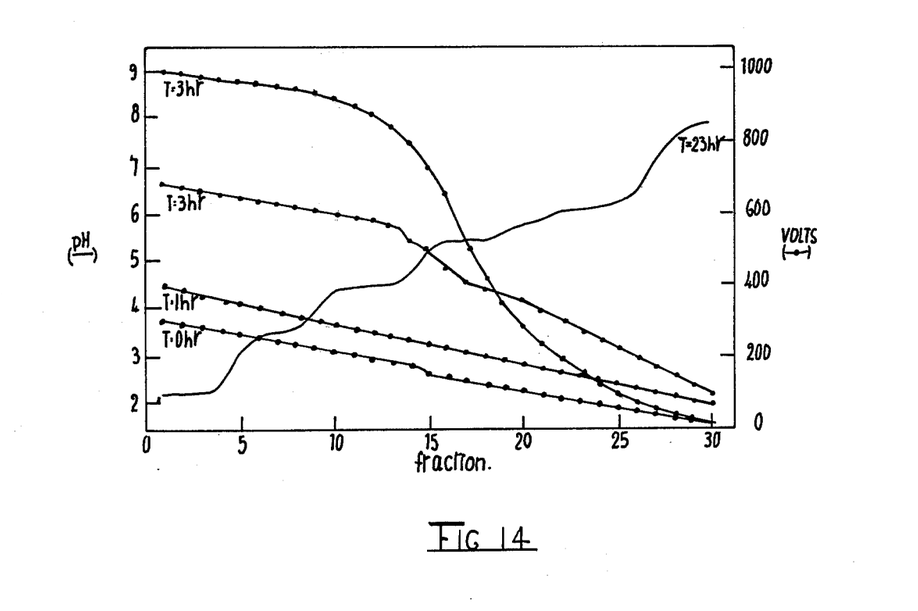

(a) The buffer system employing amphoteric and non-amphoteric components: MES, ACES, TES, Tricine, Bicine, Asn, Tau, Gly, GABA, GlyGly, Lactic and Propionic acids, His and Bistris, 20 mM each component (system 12): generated the pH gradient shown in FIG. 14. Under conditions of voltage regulation such that the total electrophoretic power dissipated in the gel was held at ca. 15 W, the voltage gradient change along the gel versus time showed the anticipated increase. The voltage gradient measurements at time T=0, 1, 3 and 9 hours are shown superimposed on the pH gradient in FIG. 14. After 9 hours at 1000 V, no further change in the gradients occurred under these conditions with the pH gradient remaining stable for at least 48 hours. The stability and shape of this pH gradient makes this buffer system suitable for preparative focusing experiments.

Figure 15:
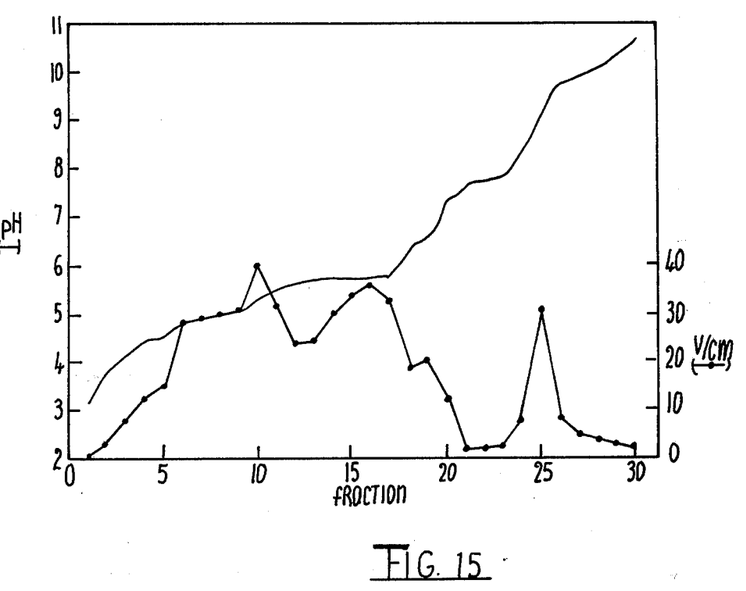
Figure 16:
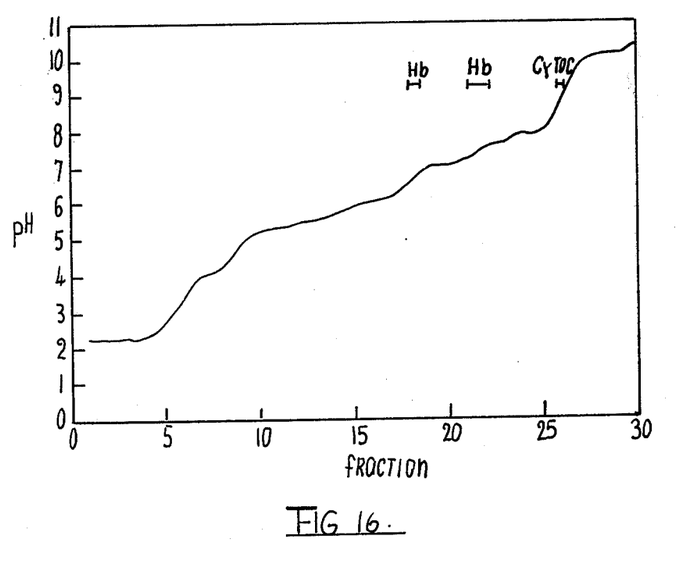
FIG. 16 is a plot of the pH gradient alone described in Example 9b following.

(b) When the non-amphoteric reagents, Tris, TEA and EA, were included with the buffer system 12, a pH gradient useful over the range 5-8.5 was generated (FIG. 15). The pH gradient of this buffer combination (system 13) remained essentially constant for the duration of electrofocusing for at least 48 hours. When the 0.2 M $H_2SO_4$ anolyte was changed to 0.1 M lactic acid in an attempt to circumvent the rapid pH change below 5 found with buffer system 13 only a small effect was witnessed (FIG. 16), similar to what is observed with 0.01 M phosphoric acid as anolyte in related systems.

EXAMPLE 9

5 g of washed and dried Sephadex G-75 was suspended in 100 $cm^3$ of the buffer of Example 8 and the suspension was poured into the gel tray of a LKB Multiphor apparatus, between filter paper wicks soaked in the same buffer. Excess buffer was removed from the gel suspension by placing filter paper strips in contact with the electrode wicks. The sample solution was stirred into the gel near to the centre of the slab using a stainless steel sample applicator frame. The applicator frame (dimensions $1 \times 11 \times 2$ cm) resting just above and across the gel bed, permitted a uniform loading of the sample. Anode and cathode wicks soaked in 0.2 M $H_2SO_4$ and 0.2 M KOH, respectively, were placed on top of the end wicks and the gel tray was placed onto the cooling plate of the Multiphor apparatus. A layer of kerosine between the tray and the cooling plate was used to ensure efficient heat transfer. The voltage was varied manually throughout the experiment to limit the power dissipated in the gel at all times to ca. 15 W (2) Focusing was carried out at ambient temperatures of ca. 18° C. Voltage and current were measured with a Universal Model 8, mark III, resistivity was calculated from Ohms Law. Typical running voltages started near 200 V and were gradually increased to 1000 V.

All commercial protein samples were obtained from Sigma Chemical Company. Rabbit antisera to human serum proteins were supplied by Behringwerke AG. The sheep thyroid TSH-receptor preparation was obtained from solubilized plasma membranes. At the conclusion of the focusing experiment, a paper print of the distribution of protein zones was obtained fixed in 7.5% trichloroacetic acid, and stained with Coomassie blue G-250. The gel bed was sectioned, and pH of each section was, after the addition of water (2 $cm^3$), measured with a glass electrode on a Radiometer PHM64. Proteins were recovered from the gel sections by elution with water or 0.1 M Tris-HCl pH 7.9 buffer, dialized, and lyophilized.

On focusing the buffer of example 8 generated a pH gradient adequate for use with many proteins having pI values between 4.5 and 8. When the non-amphoteric components TEA, Tris and ethanolamine were added to the buffer of example 8, in the same concentrations, the range was extended to higher pI values and thus was suitable for more basic proteins. Provided the power dissipated in the gel was less than 15 W at all times, both the standard and the basic buffer mixtures generated useful pH gradients over electrofocusing times greater than 48 h. At higher wattages, localized heating occurred with denaturation of protein bands. Stable gradients, using either buffer system were obtained with 0.1 M of each constituent reagent and these concentrations were generally used although concentrations as low as 0.01 M with shorter focusing times, were also effective. At the completion of the focusing experiment, the protein bands were visualized using the print technique of Radola (see example 1). Even at buffer concentrations of 0.1 M these reagents caused no interference with either direct general staining techniques or alternatively zymographic methods for the localization of active enzymatic zones, e.g. lactate dehydrogenase separation. Total protein recoveries ranged from 42 to 85% for the examples discussed in this paper. Optimal conditions of recovery were not examined.

EXAMPLE 10

A mixture of bovine heamoglobin, catalase (beef liver), bovine serum albumin and ovalbumin (hen's egg) 10 mg of each in 1 $cm^3$ of the focusing buffer) was focused in the standard buffer (0.1 M) Focusing was terminated at 40 hr. The pI values of the various proteins obtained under these conditions are compared with literature values in Table 2. It can be seen that all pI values agree with those previously reported to within 0.3 pH unit and this variation can easily be accounted for by the spread in reported pI values and by the variation of pI with temperature. After sectioning and elution of all bands the total protein recovery was 68%. In a separate experiment ovalbumin and heamoglobin were electrofocused under identical conditions. The ovalbumin recovery was 85% and heamoglobin 42%. Absence of cross contamination of the eluate peaks was confirmed using the flatbed polyacrylamide gel electrofocusing technique of Beeley et al. (1972) Biochim, Biophys, Acta 285, 293-300.

TABLE 2 pI VALUES OBTAINED BY BUFFER ELECTROFOCUSING OF A MIXTURE OF OVALBUMIN, BOVINE SERUM, ALBUMIN, CATALASE AND HEAMOGLOBIN

| PROTEIN | pI (observed) | pI (literature) |
| --- | --- | --- |
| Ovalumin | 4.7 | 4.52-4.98 |
| Bovine serum albumin | 4.9 | 4.7-4.9 |
|  | 5.4 | 4.9-5.28 |
| Catalase (beef liver) | 5.6 | 5.37 |
|  | 6.4 | 6.30 |
| Bovine heamoglobin | 7.5 | 7.2 |

EXAMPLE 11

A sample of a myeloma serum (1.5 cm³, 120 mg) was focused in amphoteric/non-amphoteric buffer (0.1 M) of example 9. Focusing was terminated at 46 h and the pH gradient observed. The gel slab was sectioned into 30 fractions and each fraction eluted with distilled water, exhaustively dialyzed, and concentrated. The total protein recovery, based on $\epsilon_{280}\epsilon_{260}$ was 79%, with proteins distributed over fractions 7-25. The results of immunodiffusion analysis of each fraction against a range of antisera were that not all protein species are equally focused after this time interval, and some appeared to form multiple bands. A minimum of 12 serum components could be recognized, all of which had retained their immunological reactivity toward antiwhole human serum during the electrofocusing process.

EXAMPLE 12

A sample (280 mg) of partially purified thyroid protein exhibiting high biological binding activity for thyroid-stimulating autoantibodies, was electrofocused using the first buffer of example 10 (0.1 M) for 40.5 h. The gel slab was sectioned and the proteins eluted from each section were dialyzed against distilled water, freeze-dried, and assayed in the Mackenzie mouse bioassay. The activity was found to be located in fraction 1 (pI=4.3-5.1) which represents 52% of the total protein. Some protein recipitation was observed during the electrofocusing experiment of minor protein components.

The isoelectric focusing results obtained with the simple amphoteric and nonamphoteric buffer mixtures clearly indicate that these conditions are useful for the purification, on a preparative scale, of a variety of proteins.

What is claimed is:

1. A preparative electrofocusing system for preparative resolution of a sample, said system comprising a flatbed granular polysaccharide gel having a high sample-loading capacity suspended in a buffer mixture, a catholyte at one side of said flatbed gel and an anolyte at the other side thereof, and a source of direct current between said catholyte and said anolyte, said buffer mixture comprising a combination of at least four amphoteric members selected from the group consisting of: Glu, LA, PA, Pyr, MES, ADA, Bistris, MOPS, ACES, Imid, HEPES, TES, EPPS, TEA, TAPS, Glygly, Tricine, Bicine, Asn, Tris, AEPD, AMP, NH₃, His, Gly, Tau, B-Ala, EA, Lys, TA, GACA and GABA.

2. The electrofocusing system according to claim 1 wherein said polysaccharide gel is cross-linked dextran having functional ionic groups attached to glucose units of the polysaccharide chain by ether linkages.

3. The electrofocusing system of claim 2 wherein said anolyte is 200 mM H₂SO₄ and said catholyte is a 200 mM solution of KOH.

4. The electrofocusing system of claim 2 wherein said anolyte is 200 mM H₃PO₄ and said catholyte is a 200 mM solution of KOH or other alkali hydroxide.

5. The electrofocusing system of claim 2 wherein said anolyte is 1 M HCl and said catholyte is a 1 M solution of NaOH or other alkali hydroxide.

6. The electrofocusing system of claim 2 wherein said anolyte is 100 mM lactic acid and said catholyte is a 100 mM solution of KOH or other alkali hydroxide.

7. The electrofocusing system of claim 3 wherein a voltage, current and power regulator is provided to regulate the voltage, current and power applied.

8. The electrofocusing system according to any one of claims 1 to 7 wherein the said buffer comprises a mixture of 20 mM concentration each in deionized water of the following buffers: MES, ACES, TES, Tricine, Bicine, Asn, Tau, Gly, GABA, Glygly, LA, PA, His and Bistris.

9. The electrofocusing system according to any one of claims 1 to 7 wherein the said buffer comprises a mixture of 20 mM concentration each in deionized water of the following buffers: MES, ACES, TES, Tricine, Bicine, Asn, Tau, Gly, GABA, Glygly, LA, PA, His, Bistris, Tris, TEA and EA.

10. The electrofocusing system according to any one of claims 1 to 7 wherein the said buffer comprises a mixture of 20 mM concentration each in deionized water of the following buffers: Glygly, Gly, β-Ala, GABA, GACA, His, Lys, Tris, AEPD, NH₃, AMP, TEA and β-mercaptoethanol.

11. The electrofocusing system according to any one of claims 1 to 7 wherein the said buffer comprises a mixture of 20 mM concentration each in deionized water of the following buffers: Glu, MES, ACES, MOPS, HEPES, TES, EPPS, TAPS, Tricine, Bicine, Asn, Glygly and β-mercaptoethanol.

12. The electrofocusing system according to any one of claims 1 to 7 wherein the said buffer comprises a mixture of 20 mM concentration each in deionized water of the following buffers: Glygly, Gly, β-Ala, GABA, GACA, His and Lys.

13. The electrofocusing system according to any one of claims 1 to 7 wherein the said buffer comprises a mixture of 20 mM concentration each in deionized water of the following buffers: Glu, Glygly, His and Lys.

14. The electrofocusing system according to any one of claims 1 to 7 wherein the said buffer comprises a mixture of 20 mM concentration each in deionized water of the following buffers: Glu, Tau, Gly, GABA and Lys.

15. The electrofocusing system according to any one of claims 1 to 7 wherein the said buffer comprises a mixture of 20 mM concentration each in deionized water of the following buffers: Glu, Tau, GABA and Lys.

16. The electrofocusing system according to any one of claims 1 to 7 wherein the said buffer comprises a mixture of 20 mM concentration each in deionized water of the following buffers: MES, ACES, TES, Tricine, Bicine and Tau.

17. The electrofocusing system according to any one of claims 1 to 7 wherein the said buffer comprises a mixture of 20 mM concentration each in deionized water of the following buffers: MES, ACES, TES, Tau, Tricine and Bicine.

18. In an electrofocusing system including a flat-bed granular gel suspended in a buffer mixture with a catholyte at one side of said flatbed gel and an anolyte at the other side thereof, and a source of direct current between said catholyte and said anolyte, the improvement comprising a preparative electrofocusing system for preparative resolution of a sample, comprising a granular polysaccharide gel having a high sample-loading capacity suspended in a buffer mixture comprising a combination of at least four amphoteric members selected from the group consisting of: Glu, LA, PA, Pyr, MES, ADA, Bistris, MOPS, ACES, Imid, HEPES, TES, EPPS, TEA, TAPS, Glygly, Tricine, Bicine, Asn, Tris, AEPD, AMP, $NH_3$, His, Gly, Tau, B-Ala, EA, Lys, TA, GACA and GABA, said preparative electrofocusing system generating at least one long and flat pH gradient to thereby allow preparative resolution of the sample into respective constituent components.

19. In an electrofocusing system including a flatbed granular gel suspended in a buffer mixture with catholyte at one said of the flatbed gel and an anolyte at the other side thereof, and the source of direct current between said catholyte and said anolyte, the improvement comprising a preparative electrofocusing system for preparative resolution of protein mixtures, said system comprising a granular polysaccharide gel having a high protein-loading capacity suspended in a buffer mixture comprising a combination of at least four amphoteric members selected from the group consisting of: Glu, LA, PA, Pyr, MES, ADA, Bistris, MOPS, ACES, Imid, HEPES, TES, EPPS, TEA, TAPS, Glygly, Tricine, Bicine, Asn, Tris, AEPD, AMP, $NH_3$, His, Gly, Tau, B-Ala, EA, Lys, TA, GACA and GABA, said preparative electrofocusing system generating at least one long and flat pH gradient to thereby allow preparative resolution of said protein mixture into respective constituent proteins in high yield without significant loss of biological activity.

* * * * *